United States Patent [19]

Founds et al.

[11] Patent Number: 5,610,076
[45] Date of Patent: Mar. 11, 1997

[54] METHOD FOR DETECTING HEMOGLOBIN ADVANCED GLYCOSYLATION ENDPRODUCTS

[75] Inventors: Henry W. Founds, Mendham, N.J.; Michael A. Yamin, Tappan, N.Y.; Richard J. Bucala, New York, N.Y.; Anthony Cerami, Shelter Island, N.Y.

[73] Assignee: Alteon Inc., Ramsey, N.J.

[21] Appl. No.: 236,416

[22] Filed: Apr. 29, 1994

[51] Int. Cl.$^6$ ................................................. G01N 33/543
[52] U.S. Cl. ........................... 436/518; 435/79; 435/7.92; 435/962; 435/975
[58] Field of Search .................................. 435/7.9, 7.92, 435/7.93, 7.94, 975, 962; 436/518, 18

[56] References Cited

U.S. PATENT DOCUMENTS

| 4,658,022 | 4/1987 | Knowles et al. ........................ 436/548 |
| 5,254,593 | 10/1993 | Ulrich et al. ............................ 514/653 |

FOREIGN PATENT DOCUMENTS

| 33871/93 | 8/1994 | Australia . |
| 0325710 | 8/1989 | European Pat. Off. . |
| 0407860 | 1/1991 | European Pat. Off. . |
| 0559164 | 9/1993 | European Pat. Off. . |
| WO93/13421 | 7/1993 | WIPO . |

OTHER PUBLICATIONS

Makita et al. 1992. J. Biol. Chem. 267:5133.
Makita et al. 1992. Science 258:651.
Makita et al. 1991. Diabetologia 34:40.
Monnier et al. 1984. Proc. Natl. Acad. Sci. USA 81:583.
Monnier and Cerami. 1983. "Nonenzymatic glycosylation and browning of protiens in vivo" *Maillard Reaction in Food and Nutrition.* ed. G. A. Waller. American Chemical Society. pp. 431–449.
Monnier and Cerami. 1983. Biochem. Biophys. Acta 760:97.
Monnier and Cerami. 1982. Clinics in Endocrinology and Metabolism. 11:431–52.
Monnier and Cerami. 1981. Science 211:491.
Bunn et al. 1975. Biochem. Biophys. Res. Commun. 67:103.
Koenig et al. 1977. J. Biol. Chem. 252:2992.
Maillard. 1972. C. R. Acad. Sci. 154:66.

*Primary Examiner*—Mary E. Mosher
*Assistant Examiner*—Donna C. Wortman
*Attorney, Agent, or Firm*—Klauber & Jackson

[57] ABSTRACT

The present invention relates to methods for the diagnosis and monitoring of diseases and disorders associate with advanced glycosylation endproducts (AGE) formation, such as diabetes and the ageing process. In particular, the invention is directed to detecting AGE-modified hemoglobin (Hb-AGE) for the foregoing purposes, and in improved assay therefore. The method involves diluting the sample in a dilution buffer, which dilution buffer comprises an anionic protein denaturing detergent at a concentration sufficient to denature hemoglobin-AGE without interfering in binding of reagents with hemoglobin-AGE the dilution buffer may also include a non-ionic surfactant at a concentration sufficient to facilitate detection of hemoglobin-AGE; and a denaturing agent at a concentration sufficient to denature hemoglobin-AGE and increase assay sensitivity, without denaturing binding of reagents to hemoglobin-AGE. After diluting the sample in the dilution buffer, the sample is contacted with means for detecting the presence of hemoglobin-AGE in the sample, and the presence of hemoglobin-AGE in the sample is detected with the detection means. Dilution buffers and kits for practicing the invention are also provided. In specific examples, the level of AGE in hemoglobin in samples from human and rat normal subjects and diabetic subjects is detected. The results obtained from human samples show a high degree of correlation between the level of hemoglobin-AGE in a sample and the level of hemoglobin-$A_{1c}$ in a sample. Most importantly, the invention is used to detect the "aminoguanidine effect," which is the decrease in the level of hemoglobin-AGE in a sample from a subject undergoing therapy with the AGE-inhibitor aminoguanidine.

25 Claims, 4 Drawing Sheets

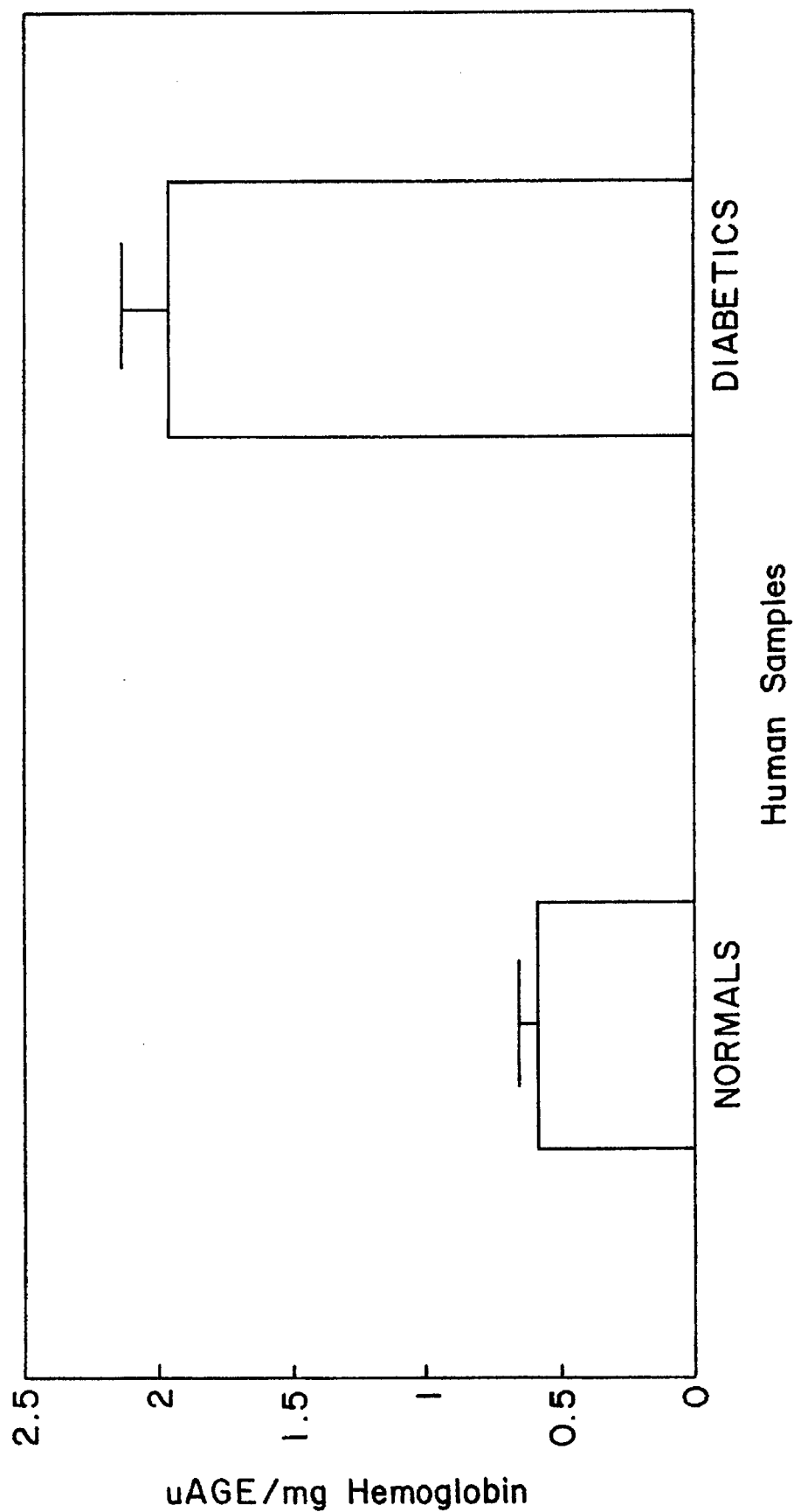

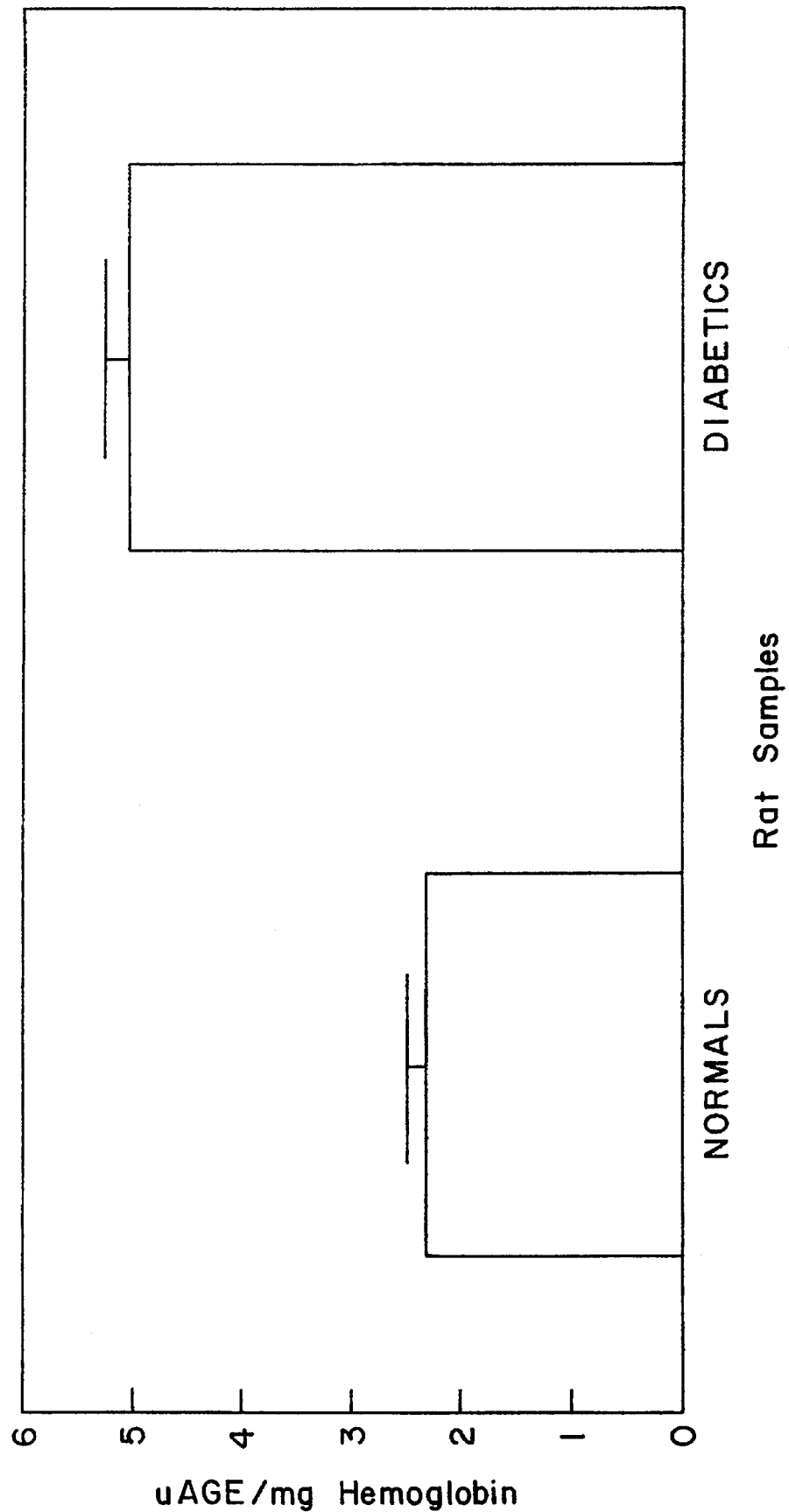

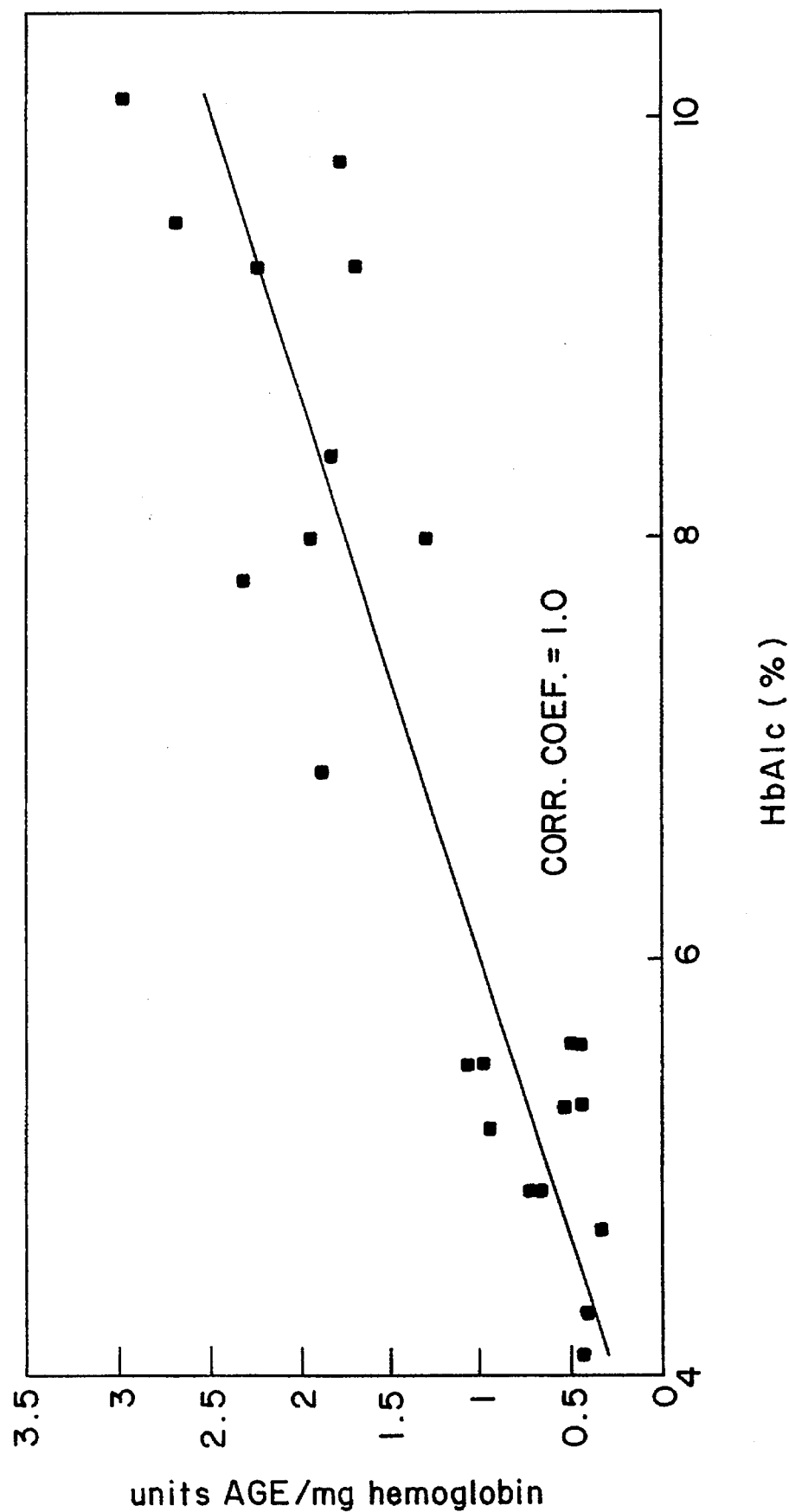

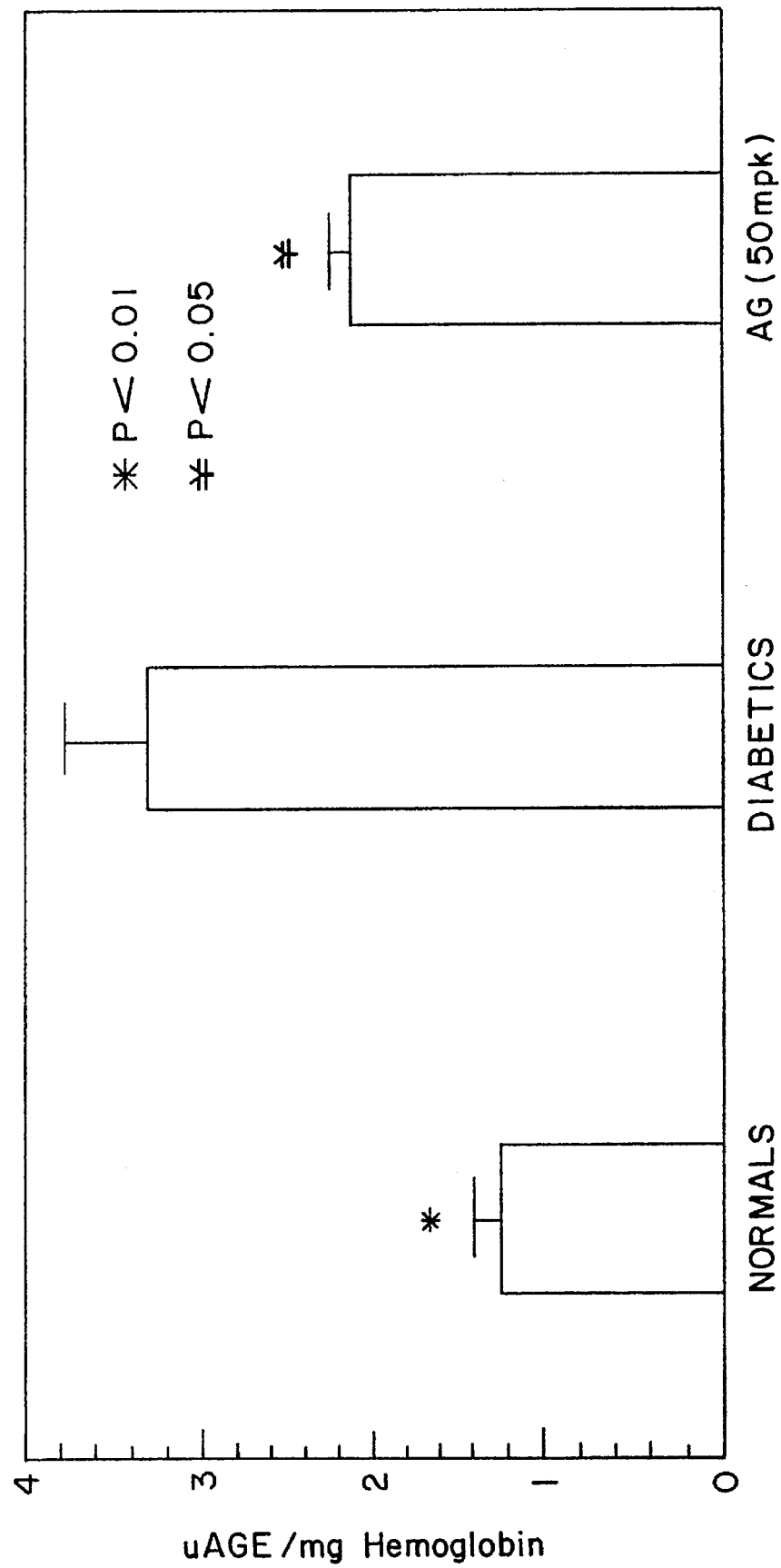

METHOD FOR DETECTING HEMOGLOBIN ADVANCED GLYCOSYLATION ENDPRODUCTS

FIELD OF THE INVENTION

The present invention relates to method for diagnosis and monitoring of diseases and disorders associated with advanced glycosylation endproducts (AGE) formation. Accordingly, the invention relates to diagnosing and monitoring diabetes and the ageing process. In particular, the invention is directed to detecting AGE-modified hemoglobin (Hb-AGE) for the foregoing purposes, and in improved assay therefore.

BACKGROUND OF THE INVENTION

The reaction between glucose and proteins has been known for some time. Its earliest manifestation was in the appearance of brown pigments during the cooking of food. In 1912, Maillard observed that glucose or other reducing sugars react with amino acids to form adducts that undergo a series of dehydrations and rearrangements to form stable brown pigments (Maillard, 1912, C. R. Acad. Sci. 54:66–68).

Thus, the nonenzymatic reaction between glucose and the free amino groups on proteins to form a stable amino, 1-deoxy ketosyl adduct, known as the Amadori product, has been shown to occur with hemoglobin, wherein the reaction of glucose with the amino terminus of the β-chain of hemoglobin forms the adduct known as hemoglobin $A_{1c}$. The reaction has also been found to occur with a variety of other body proteins, such as lens crystallin, collagen and nerve proteins (see Bunn et al., 1975, Biochem. Biophys. Res. Commun. 67:103–109; Koenig et al., 1975, J. Biol. Chem. 252:2992–2997; Monnier and Cerami, in *Maillard Reaction in Food and Nutrition*, ed. Waller, G. A., American Chemical Society 1983, pp. 431–448; and Monnier and Cerami, 1982, Clinics in Endocrinology and Metabolism 11:431–452).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years (see Monnier and Cerami, 1981, Science 211:491–493; Monnier and Cerami, 1983, Biochem. Biophys. Acta 60:97–103; and Monnier et al., 1984, Proc. Natl. Acad. Sci. USA 81:583–587).

Glucose and other reducing sugars attach non-enzymatically to the amino groups of proteins in a concentration-dependent manner. Over time, these initial Amadori adducts can undergo further rearrangements, dehydrations and cross-linking with other proteins to accumulate a family of complex structures referred to as Advanced Glycosylation Endproducts (AGEs). Substantial progress has been made toward the elucidation of the role and clinical significance of advanced glycosylation endproducts, so that it is now acknowledged that many of the conditions heretofore attributed to the aging process or to the pathological effects of diseases such as diabetes, are attributable at least in part to the formation of AGEs in vivo.

AGE accumulation can be indicative of protein half-life, sugar concentration, or both. These factors have important consequences. Numerous studies have indicated that AGEs play an important role in the structural and functional alterations which occur during aging and in chronic disease. Additionally, advanced glycosylation endproducts are noted to form more rapidly in diabetic and other diseased tissue than in normal tissue.

Hb-AGE has been found to be predictive of aging or disease progression over the long term (International Patent Publication No. WO 93/13421 by Bucala, published Jul. 8, 1993; Makita et at., 1992, Science 258:651–653). Hb-AGE measurements provide an appropriate index of long-term tissue modification by AGEs and are useful in assessing the contribution of advanced glycosylation to a variety of diabetic and age-related complications. While hemoglobin $A_{1c}$ ($HbA_{1c}$) has been reported as predictive of the extent of glycation on the hemoglobin β chain, $HbA_{1c}$ is only a reversible intermediate in the advanced glycosylation pathway and numerous other intermediates are believed to exist. Hb-AGE, as an irreversible adduct, is a superior measure of disease progression, drug effectiveness, etc.

Hb-AGEs are used to more readily correlate the progression of disease and longer term control of blood sugar levels. $HbA_{1c}$ is a reversible intermediate, and reaches equilibrium with glucose over a 3–4 week period. Hence, levels of $HbA_{1c}$ only reflect blood glucose only during this short time period. Hb-AGE, in contrast, is an irreversible adduct and reflects blood sugar over the lifespan of hemoglobin. Thus, the effectiveness of treatment for AGE-related diseases or disorders can also be determined from the level of Hb-AGE in samples. Thus, the reduction in Hb-AGE levels as a result of aminoguanidine therapy is a primary example of the successful pharmacological inhibition of advanced glycosylation in human subjects.

Prior to the instant invention, detection of Hb-AGEs required a complex assay format, that included TCA precipitation of the hemoglobin from the hemolysate, followed by centrifugation to separate the precipitated protein from the supernatant liquid fraction. Resolution of the precipitate was accomplished by adding sodium hydroxide at high pH (pH>11), followed by pH adjustment with 0.3M $KH_2PO_4$, pH 7.4 buffer (Makita et al., 1991, Diabetologia 34:40–45). After pH adjustment to about 7.8, some of the hemoglobin precipitates out of solution, thus requiring a separation step prior to assay of the liquid fraction. In short, the current protocol complex, is cumbersome, time consuming, subject to and generally not applicable to a clinical laboratory setting.

Accordingly, there is a need in the art for a simpler, faster, and milder sample treatment protocol to facilitate testing for Hb-AGE in clinical laboratory settings.

There is a further need in the art for kits containing the reagents necessary to perform such assays.

The citation of references herein shall not be construed as an admission that such is prior art to the present invention.

SUMMARY OF THE INVENTION

The present invention is directed broadly to a method for detecting the presence of hemoglobin-AGE in a sample. The method involves diluting the sample in a dilution buffer, which dilution buffer comprises an anionic protein denaturing detergent at a concentration sufficient to denature hemoglobin-AGE without interfering in binding of reagents with hemoglobin-AGE. Preferably, the dilution buffer further comprises a non-ionic surfactant at a concentration sufficient to facilitate detection of hemoglobin-AGE; and a polar denaturing agent at a concentration sufficient to denature hemoglobin-AGE and increase assay sensitivity, without denaturing binding of reagents to hemoglobin-AGE. After diluting the sample in the dilution buffer, the sample is contacted with means for detecting the presence of hemoglobin-AGE in the sample, and the presence of hemoglobin-AGE in the sample is detected with the detection means. The sample can be assayed directly after dilution.

In specific aspects, the concentration of anionic protein denaturing detergent in the dilution buffer ranges from about 0.04% to about 0.16% (w/v). The concentration of non-ionic surfactant, if present, ranges from about 0.005% to about 0.1% (w/v); and the concentration of the denaturing agent, if present, is between about 0.5M to about 3M.

In a specific preferred embodiment, the anionic protein denaturing detergent is sodium dodecyl sulfate. In a further specific preferred embodiment, the non-ionic surfactant is a polyoxyethylene ester, in particular Triton X-100 polyoxyethylene ester, and the denaturing agent is urea.

The best mode contemplated by the inventor for practicing the invention uses a dilution buffer in which the concentration of sodium dodecyl sulfate is about 0.08%, the concentration of Triton X-100 polyoxyethylene ester is selected from the group consisting of about 0.01% and about 0.04%, and the concentration of urea is about 2M.

Preferably, the dilution buffer is buffered to between about pH 7 to about pH 8, and contains salts at a concentration approximating physiological ionic strength.

In a further embodiment, the invention provides a method for quantitating the amount of hemoglobin-AGE in a sample. Quantitation can be accomplished by detecting the presence of hemoglobin-AGE in the sample as described above. The extent of binding of a binding partner to hemoglobin-AGE, or other means for detecting the presence of hemoglobin-AGE, can be quantitated. The extent of detection corresponds to the amount of hemoglobin-AGE in the sample.

The invention further provides a method for detecting or diagnosing the presence of a disease associated with elevated hemoglobin-AGE levels in a mammalian subject by comparing the amount or level of hemoglobin-AGE detected in a sample to a level of hemoglobin-AGE normally present in the mammalian subject. An increase in the level of hemoglobin-AGE as compared to normal levels indicates a disease associated with elevated levels of hemoglobin-AGE.

In another aspect, the invention provides a method for monitoring the course of a disease associated with elevated hemoglobin-AGE levels in a mammalian subject. The level or amount of hemoglobin-AGE in a series of samples obtained at different time points from a mammalian subject is determined, as described above. An increase in the level of hemoglobin-AGE over time indicates progression of the disease; a decrease in the level of hemoglobin-AGE over time indicates regression of the disease.

In yet a further aspect, the invention provides a method for monitoring a therapeutic treatment of a disease associated with elevated hemoglobin-AGE levels in a mammalian subject. The level or amount of hemoglobin-AGE in samples obtained at different time points from a mammalian subject undergoing a therapeutic treatment for a disease associated with elevated hemoglobin-AGE levels is determined. A decrease in the level of AGEs over time indicates an effective therapeutic outcome.

In particular, the invention provides a preferred method for titrating a dosage of an inhibitor of AGE formation to determine the optimum dosage. The level or amount of hemoglobin-AGE in a series of samples obtained at different time points from a mammalian subject receiving progressively larger doses of an inhibitor of AGE formation over the time points is evaluated. An optimum dosage of the inhibitor is a dosage above which no further decrease in the level of hemoglobin-AGE is observed.

In still another aspect, the invention provides a method for monitoring the long term glucose level in a mammalian subject. The level or amount of hemoglobin-AGE in a sample from a mammalian subject is determined. The level or amount of hemoglobin-AGE is indicative of the long term glucose level in the subject.

The methods of the present invention are achieved by dilution of the sample in the dilution buffer of the invention. Accordingly, the present invention further provides a dilution buffer. The dilution buffer of the invention comprises an anionic protein denaturing detergent; a non-ionic surfactant; and a polar denaturing agent. These reagents can be provided in a concentrate, for dilution such that the anionic protein denaturing detergent is present at a concentration sufficient to denature hemoglobin-AGE without interfering in binding of reagents with hemoglobin-AGE; the non-ionic surfactant is present at a concentration sufficient to facilitate detection of hemoglobin-AGE; and the denaturing agent is present at a concentration sufficient to denature hemoglobin-AGE and increase assay sensitivity, without denaturing binding of reagents to hemoglobin-AGE. Preferably, the dilution buffer is prepared such that the concentration of anionic protein denaturing detergent in the dilution buffer ranges from about 0.04% to about 0.16% (w/v); the concentration of non-ionic surfactant ranges from about 0.005% to about 0.1% (w/v); and the concentration of the denaturing agent is between about 0.5M to about 3M. In another preferred aspect, the anionic protein denaturing detergent is sodium dodecyl sulfate, the non-ionic surfactant is Triton X-100 polyoxyethylene ester, and the denaturing agent is urea. In the most preferred aspect of the invention, which is the best mode contemplated by the inventors for practicing the invention, the concentration of sodium dodecyl sulfate is about 0.08%, the concentration of Triton X-100 polyoxyethylene ester is selected from the group consisting of about 0.01% and about 0.04%, and the concentration of urea is about 2M.

In a further embodiment, the dilution buffer is buffered to between about pH 7 to about pH 8, and contains salts at a concentration approximating physiological ionic strength.

In a further aspect, the present invention relates to a kit for detecting the presence of hemoglobin-AGE in a sample. The kit of the invention comprises a dilution buffer as described above, in concentrated or ready-to-use form; means for detecting the presence of hemoglobin-AGE; other reagents; and directions for use of said kit.

In an Example, infra, the present invention provides for detection of the level of AGE in hemoglobin in samples from normal subjects and diabetic subjects. Samples from both humans and rats were successfully tested using the method of the invention. Furthermore, the results obtained from human samples show a high degree of correlation between the level of hemoglobin-AGE in a sample and the level of hemoglobin-$A_{1c}$ in a sample. Most importantly, the assay of the instant invention can be used to detect the "aminoguanidine effect," which is the decrease in the level of hemoglobin-AGE in a sample from a subject undergoing therapy with the AGE-inhibitor aminoguanidine. This effect cannot be detected by measuring the level of hemoglobin-$A_{1c}$, since aminoguanidine, or other inhibitors of AGEs, do not affect hemoglobin-$A_{1c}$ levels. The so called "aminoguanidine effect" applies to other AGE-inhibitors as well.

Thus, the present invention advantageously provides for monitoring the efficacy of a therapy for preventing advanced glycosylation endproduct formation, as well as a more sensitive test for diagnosis of an AGE-associated disease or disorder.

Accordingly, it is an object of the present invention to provide an improved assay for hemoglobin-AGE.

It is a further object of the invention to provide a dilution buffer that increases the speed, ease, and simplicity of assays for hemoglobin-AGE.

It is a yet another object of the invention to provide a buffer that enhances immuno-detection of hemoglobin-AGE.

Yet a further object of the invention is to provide kits for detecting the presence of hemoglobin-AGE in a sample.

These and other objects of the invention are addressed and will be better understood by reference to the following drawings and detailed description of the invention.

BRIEF DESCRIPTION OF THE DRAWINGS

FIGS. 1A and 1B presents the level of AGE modification of hemoglobin. The samples were pretreated with 0.08% SDS, 0.04 % or 0.01% Triton X-100, and 2M urea in the sample diluent prior to testing in an antibody ELISA assay for the level of AGE modification. The data are reported as units of AGE per mg of hemoglobin in samples from diabetic and normal subjects ± standard error of the mean (SEM). The amount of AGE was determined using an ELISA assay developed earlier (Makita et al., 1992, J. Biol. Chem. 267:5133–38; International Patent Publication WO 93/13421); the concentration of protein (which consists mostly of hemoglobin) was determined with the Lowry reagent using purified bovine serum albumin as a standard (Lowry et al., 1951, J. Biol. Chem. 193:265). (A) Samples were obtained from 11 normal and 11 diabetic humans. The hemoglobin $A_{1c}$ levels for the normals were 4.9±0.52, and for diabetics were 8.3±1.49. A concentration of 0.04% Triton was used to pre-treat human samples. (B) Samples were obtained from 10 normal and 10 diabetic rats. Diabetes was induced in rats by treatment with streptozocin, and hyperglycemia was confirmed by assaying blood glucose.

FIG. 2 presents data which demonstrate the correlation between measurement of hemoglobin-AGE (units of AGE per mg of hemoglobin) according to the present invention versus the level of hemoglobin $A_{1c}$ (percentage of total hemoglobin). The correlation was performed with 22 human samples (the same samples as shown in FIG. 1A).

FIG. 3 presents data that demonstrate the sensitivity of the present assay to detecting the hemoglobin effect. The level of AGE-hemoglobin (units of AGEs per mg of hemoglobin) was measured after pretreatment of samples according to the present invention. Samples were obtained from normal rats, induced diabetic rats, and diabetic rats that received 50 mg per kg of aminoguanidine; each sample group included 10 members. Statistically significant differences in the level of Hb-AGE were observed between normal and diabetic rats ($p<0.01$), and between aminoguanidine-treated and diabetic rats ($p<0.05$).

DETAILED DESCRIPTION OF THE INVENTION

The present invention relates to an improved assay for hemoglobin-AGE. In particular, the invention discloses a dilution buffer containing an anionic protein denaturing detergent, such as sodium dodecyl sulfate. Preferably, the dilution buffer further comprises a non-ionic surfactant, such as polyoxyethylene esters like Triton X-100, and a polar denaturant, such as urea. Dilution of hemolysate in this dilution buffer significantly increases the simplicity and speed of assays for hemoglobin-AGE.

As used herein, the term "AGE-" refers to the compound which it modifies as the reaction product of either an advanced glycosylation endproduct or a compound which forms AGEs and the compound so modified, such as the bovine serum albumin (BSA). Thus, AGEs include, but are not limited to, AGE-proteins (such as BSA-AGE), AGE-lipids, AGE-peptides, and AGE-DNA. AGE polypeptides or AGE proteins can be formed in vitro or in vivo by reacting a polypeptide or protein with an AGE, such as AGE-peptide, or with a compound such as a reducing sugar, e.g., glucose, until the polypeptide or protein is modified to form the AGE-polypeptide or protein.

The term "glycosylation" is used herein to refer to the non-enzymatic reaction of reducing sugars with a nucleophile, in particular an amine group, on a polypeptide or protein, such as hemoglobin, a lipid, or DNA, which leads to formation of AGEs. These processes are well known in the art, as described above. Recently, the term "glycation" has become more favored to refer to non-enzymatic glycosylation processes. Thus, the term "glycosylation," as specifically defined herein, and "glycation" are equivalent.

As stated above, according to the present invention, a sample containing red blood cells or hemoglobin from a subject is treated by dilution in a dilution buffer, e.g., buffer containing sodium dodecyl sulfate, Triton X-100, and urea. The sample may be blood, or red blood cells isolated from blood, that has been treated to hemolyze the red blood cells. Alternatively, the sample may be hemoglobin isolated from red blood cells.

Although not intending to be limited by any particular theory or hypothesis, it is believed that moderate denaturation of hemoglobin exposes additional AGE epitopes to antibody binding, thus significantly increasing the sensitivity of an immunoassay for Hb-AGE compared to untreated samples.

According to the invention, samples can be obtained from any source, including in vitro or in vivo sources. In particular, the instant invention contemplates assays on a sample from an animal, and more preferably, from a mammal, including humans, as well as mammals such as dogs, cats, horses, cows, pigs, guinea pigs, mice, and rats. Thus, the present invention provides for monitoring AGE levels in human and veterinary medicine.

The concentration of anionic protein denaturing detergent, such as SDS, in the dilution buffer is sufficient to denature hemoglobin-AGE without interfering in immunological binding or causing detachment or elution of a solid phase reagent in a solid phase immunoassay. Accordingly, the concentration of anionic protein denaturing detergent can range from about 0.04% to about 0.16% (w/v), depending on the stability of the detection assay, e.g., antibody binding. Preferably, the anionic protein denaturing detergent is SDS, and the concentration of SDS is about 0.08%.

In addition to SDS, the invention further contemplates use of analogous detergents that interact with and effectively denature proteins. Although SDS has been found to be the most useful protein denaturing detergent, other such detergents, although less effective than SDS for denaturing proteins, can be used according to the present invention. Obvious choices include $C_8$ to $C_{20}$ hydrocarbon acyl sulfate salts, i.e., SDS analogs. Substitution of a different anionic protein denaturing may require retesting to determine an optimal concentration, which merely requires straightforward experimentation.

The concentration of non-ionic surfactant, if any, such as Triton X-100, in the dilution buffer is sufficient to facilitate detection of hemoglobin-AGE in a sample. The non-ionic detergent may function, in part, to buffer harsh effects of the anionic detergent. In a specific embodiment, the non-ionic surfactant is the polyoxyethylene ester Triton X-100, and the concentration of Triton X-100 ranges from about 0.005% to about 0.1% (w/v). In a preferred aspect of the invention, the concentration of Triton X-100 is approximately 0.01% for samples from rats, and 0.04% for samples from humans. Optimal concentration for samples from other animals, for different AGE-specific antibodies, and for the choice of anionic detergent can be readily determined using standard experimental techniques.

The invention further contemplates use of an analogous non-ionic surfactant in place of Triton X-100. A non-ionic surfactant to be substituted for Triton X-100 may be tested to determine an optimal concentration; such testing involves straightforward experimentation.

The concentration of a polar denaturing agent in the dilution buffer is sufficient to denature the Hb-AGE or stabilize and maintain detergent-denatured Hb-AGE in a denatured state, and increase assay sensitivity, without denaturing immunological reagents used to detect the presence of Hb-AGE in a sample. In a specific aspect, the denaturant is urea, in a concentration of between about 0.5M to about 3M. Preferably, the concentration of urea is 2M. Furthermore, the invention contemplates use of other polar denaturing reagents, such as guanidine-HCl, at a suitable concentration in place of urea.

Preferably, the dilution buffer is pH-buffered and ionic strength controlled. For example, the dilution buffer may contain a physiological concentration of sodium chloride, or other salts, as well as buffers to maintain pH of the dilution solution between about pH 5 and about pH 9. Preferably, the pH of the buffer is about pH 7 to about pH 8; more preferably, the pH is about pH 7.4. In a specific embodiment, infra, the dilution buffer is a sodium phosphate buffered solution containing sodium chloride. It is preferable not to use potassium salts in the dilution buffer, since it is known that potassium ion can induce precipitation of SDS. Another suitable buffer salt is Tris-HCl.

A sample containing hemoglobin can be diluted from about 10-fold to about 100-fold with dilution buffer prior to conducting an immunoassay to detect Hb-AGEs. Alternatively, the sample can be diluted so that the protein concentration (most of the protein being hemoglobin) ranges from about 0.1 mg/ml to about 10 mg/ml. In a specific embodiment, infra, a hemolysate sample is diluted 40-fold in the dilution buffer of the invention prior to conducting the immunoassay. In the example, infra, the concentration of protein in the sample is approximately 1–2 mg/ml, as determined by the Lowry assay, using BSA as a protein standard (Lowry et al., 1951, J. Biol. Chem. 193:265).

The present invention can enhance many of the immunoassay or immunoassay-type formats that can be used to detect the presence of, and measure the quantity of, hemoglobin-AGE, by increasing the accessibility of AGE-epitopes present on hemoglobin-AGE. As used herein, the terms "means for detecting" and "means for quantitating" hemoglobin-AGE refer to detection or quantitation of hemoglobin-AGE in any such immunoassay-type format. Generally, such means comprise contacting a sample with one or more binding partners of hemoglobin-AGE, followed by detection of binding of the one or more binding partners to hemoglobin-AGE in the sample, and, if desired, quantitation (measuring the quantity) of binding that occurs. Binding partners include, but are not limited to, antibodies to hemoglobin, antibodies to AGEs, receptors for AGEs, small molecules that bind either hemoglobin or AGEs, and the like. At least one such binding partner must be specific for an AGE. Detection of specific binding of a binding partner of hemoglobin-AGE with Hb-AGE in the sample is indicative of the presence of Hb-AGE in the sample.

Accordingly, once a sample containing hemoglobin has been diluted in the dilution buffer of the invention, the presence of Hb-AGE can be determined using many formats of immunological assay means, e.g., using well known techniques such as but not limited to radioimmunoassay, ELISA (enzyme-linked immunosorbant assay), "sandwich" immunoassays (in particular ELISA assays), competitive assays (in particular competitive ELISA assays), immunoradiometric assays, precipitation reactions, immunofluorescence assays, protein A assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled.

In a specific embodiment, a sandwich assay format is used, in which an anti-AGE antibody is attached to the solid phase, and an anti-hemoglobin antibody (either labeled directly or detected with a secondary labeled antibody) is used to detect binding of Hb-AGE with the anti-AGE antibody. In another embodiment, the anti-hemoglobin antibody can be attached to the solid phase, and an anti-AGE antibody used to bind any AGE epitopes present on the hemoglobin molecules bound to the anti-hemoglobin antibody.

As used herein, the term "antibody" refers to polyclonal, monoclonal, chimeric, and single chain antibodies, as well as Fab fragments (F(ab')$_2$, F(ab), Fv, etc.), and an Fab expression library.

The amount of hemoglobin-AGE in a sample can be determined quantitatively. For example, the extent of binding can be quantitated, and the amount of Hb-AGE determined by extrapolation from a standard curve. In a specific aspect, a standard amount of hemoglobin-AGE can be provided in a kit of the invention for use as a standard. In another embodiment, the amount of AGE (e.g., units of AGE) can be determined by comparison with a standard amount, such as a BSA-AGE sample as described in the examples, infra.

In a specific embodiment, the assay described in Makita et al. (1992, J. Biol. Chem. 267:5133–38; see also International Patent Publication No. WO 93/13421) can be used to detect the presence of Hb-AGEs in a sample prepared according to the present invention.

Kits

In a further embodiment of this invention, commercial test kits suitable for use by medical or clinical technologists or specialists may be prepared to determine the presence or absence of hemoglobin-AGEs. Such kits will include at least a dilution buffer of the invention, and means for detecting the presence of hemoglobin-AGE as described supra. The dilution buffer can be provided in concentrated form, which requires the addition of water or buffer to bring the components of the buffer to their appropriate concentration. Providing the dilution buffer in concentrated form advantageously reduces the weight and size of the kit, and thus is more cost effective.

The contents of the kit are preferably incorporated in a package, such as cardboard or plastic packaging material, which is dimensioned to hold all of the components of the kit. Each component can be held in separate containers, such as glass or plastic vials, for use or dilution prior to use.

In accordance with the testing techniques discussed above, one class of such kits will contain at least a binding partner of an AGE epitope and dilution buffer of the invention comprising an anionic protein denaturing detergent, a non-ionic detergent, and a denaturant, as described above, and means for detecting binding of the binding partner of an AGE epitope to an AGE epitope present in the sample diluted with the dilution buffer according to the invention.

The kit may also contain directions for conducting an assay in accordance with the method selected, e.g., "competitive," "sandwich," "DASP" and the like. The kits may also contain peripheral reagents such as buffers, stabilizers, etc.

Accordingly, a test kit may be prepared for the demonstration of the presence, quantity or activity of AGEs, comprising:

(a) a labeled specifically reactive component obtained by the direct or indirect attachment of a binding partner of an AGE epitope or a specific binding partner thereto, to a detectable label;

(b) a dilution buffer, in concentrated or ready-to-use form, comprising an anionic protein denaturing detergent, a non-ionic detergent, and a polar denaturant;

(c) other reagents; and (d) directions for use of said kit.

More specifically, the diagnostic test kit may comprise:

(a) a known amount of a first binding partner to an AGE epitope as described above, generally bound to a solid phase to form an immunosorbent;

(b) a second binding partner to an AGE epitope or to hemoglobin, which second binding partner is labelled;

(c) a dilution buffer, in concentrated or ready-to-use form, comprising an anionic protein denaturing detergent, a non-ionic surfactant, and a polar denaturant;

(d) if necessary, other reagents; and (e) directions for use of said test kit.

In another specific embodiment, a diagnostic test kit may comprise:

(a) a known amount of a first binding partner to hemoglobin as described above, generally bound to a solid phase to form an immunosorbent;

(b) a second binding partner to an AGE epitope, which second binding partner is labelled;

(c) a dilution buffer, in concentrated or ready-to-use form, comprising an anionic protein denaturing detergent, a non-ionic surfactant, and a polar denaturant;

(d) if necessary, other reagents; and (e) directions for use of said test kit.

In another embodiment, a diagnostic test kit may comprise:

(a) a binding partner of an AGE epitope, generally associated with a solid phase to form an immunosorbent;

(b) a known quantity of a labelled AGE that is capable of binding to the binding partner of an AGE epitope;

(c) a dilution buffer, in concentrated or ready-to-use form, comprising an anionic protein denaturing detergent, a non-ionic surfactant, and a polar denaturant;

(d) if necessary, other reagents; and (e) directions for use of said test kit.

In another embodiment, a diagnostic test kit may comprise:

(a) an AGE, generally associated with a solid phase to form an immunosorbent;

(b) a known quantity of a labelled binding partner of an AGE epitope that is capable of binding to the AGE immunosorbent;

(c) a dilution buffer, in concentrated or ready-to-use form, comprising an anionic protein denaturing detergent, a non-ionic surfactant, and a polar denaturant;

(d) if necessary, other reagents; and (e) directions for use of said test kit.

The test kits of the invention can comprise an AGE standard for quantitating the amount of AGE in a sample. In a specific embodiment, BSA-AGE is used as an AGE standard.

Preferably, in a test kit of the invention, the binding partner of an AGE epitope is an antibody to an AGE, e.g., as described above (see Makita et al., 1992, supra; International Patent Publication No. WO 93/13421).

Preferably, in a test kit of the invention that comprises an AGE, the AGE is BSA-AGE as described above and in the examples, infra.

In a preferred embodiment, the dilution buffer comprises SDS, Triton X-100, and urea in the concentrations that are disclosed supra.

Monitoring Treatment to Prevent AGE Formation

The hemoglobin-AGE assay of the present invention is particularly well suited to monitor the aminoguanidine, or other AGE-inhibitor, effect in a large scale study or trial, since the assay in fast and simple. Similarly, the assay of the present invention can provide for monitoring the course of therapy of any product expected to inhibit AGE formation. In particular, the present method for detecting hemoglobin-AGE provides for carefully titrating the therapeutic dose of an AGE-inhibitor.

In a particular aspect, the invention provides for titrating the optimum dosage of an agent that inhibits AGE formation. Titration of the optimum dosage allows a physician to select a dosage with maximum benefit for a patient, while minimizing the risk of side effects. Since metabolic pathways and rates of clearance differ from one individual to another, the optimum dose of a therapeutic agent can vary from one person to another. The term "optimum" when used to modify "dose" should not be confused with the term "effective"; a dosage of a therapeutic agent can be effective without being the optimum dose.

Thus, the invention provides for monitoring the effect of administration of agents that block the post-glycosylation step, i.e., the formation of fluorescent or crosslinking chromophores whose presence is associated with, and leads to, the adverse sequelae of glycosylation. An ideal agent would prevent the formation of a chromophore and its associated cross-links of proteins to proteins and trapping of proteins on the other proteins. The ideal agent would prevent or inhibit the long-term, post-glycosylation steps that lead to the formation of the ultimate advanced glycosylation end products that are a direct cause of AGE-associated pathology.

An inhibitor of the formation of AGEs includes compounds that react with a carbonyl moiety of an early glycosylation product. Representative of such advanced glycosylation inhibitors are aminoguanidine, lysine and α-hydrazinohistidine. In a specific embodiment, the inhibitor is aminoguanidine (AG) and derivatives thereof. Pharmaceutical compositions and methods involving AG and derivatives thereof are well known, as described in U.S. Pat. Nos. 4,758,583, issued Jul. 19, 1988; No. 4,908,446, issued Mar. 13, 1990; No. 4,983,604, issued Jan. 8, 1991; No. 5,100,919, issued Mar. 31, 1992; No. 5,106,877, issued Apr. 21, 1992; No. 5,114,943, issued May 19, 1992; No. 5,128,360, issued Jul. 7, 1992; No. 5,130,324, issued Jul. 14, 1992; No. 5,130,337, issued Jul. 14, 1992; No. 5,137,916, issued Aug. 11, 1992; No. 5,140,048, issued Aug. 18, 1992; No. 5,175,192, issued Dec. 29, 1992; No. 5,218,001, issued Jun. 8, 1993; No. 5,221,683, issued Jun. 22, 1993; No. 5,238,963, issued Aug. 24, 1993; No. 5,243,071, issued Sep. 7, 1993; and No. 5,254,593, issued Oct. 19, 1993. Other inhibitors of AGE formation are described in U.S. applications Ser. No. 07/652,575, filed Feb. 8, 1991; Ser. No. 07/889,141, filed May 27, 1992; Ser. No. 07/896,854, filed May 15, 1992; Ser. No. 07/986,661, filed Dec. 8, 1992; Ser. No. 07/986,662, filed Dec. 8, 1992; Ser. No. 08/027,086, filed Mar. 5, 1993; and Ser. No. 08/095,095, filed Jul. 20, 1993. Each of the foregoing patents and patent applications is specifically incorporated herein by reference in its entirety.

The invention may be more completely understood by reference to the following non-limiting example, which is provided solely as exemplary of a specific embodiment of the invention.

EXAMPLE: Hemoglobin AGE Assay

Materials and Methods

Pretreatment Buffer. SDS/Triton/Urea Hemolysate pretreatment buffer (1 liter) was prepared as follows:

A sodium phosphate (0.02M) buffer solution was prepared by adding 0.91 g of sodium monobasic (monohydrate); 1.902 g of sodium dibasic (anhydrous); 8 g of sodium chloride, and 0.2 g of sodium azide to 800 ml of distilled water.

To the above buffer (800 ml) were added 120.12 gm of urea (2M final concentration); 0.8 g of SDS (0.08%) samples, and 0.4 or 0.1 g of Triton X-100 (yielding concentrations of 0.04%, for human samples, or 0.01% for rat samples). The pH of the solution was adjusted to 7.4 and the volume was brought to 1 liter with distilled water.

Sodium phosphate buffer was also prepared as described above, without including urea, SDS and Triton X-100.

Preparation of the Hemolysate. Red blood cells were prepared using a distilled water/toluene extraction procedure. Briefly, red blood cells (RBCs) were separated from whole blood collected in a heparinized tube by centrifugation at 2-3000 rpm for 10 min. The RBCs were washed by resuspension in sterile isotonic saline (0.85%) in a volume approximately equal to the plasma, and repacked by centrifugation as described above. RBCs were stored for up to one week at 4° C. in buffered saline after two washing steps that included 30 min soaks in the wash buffer. RBCs could be stored for more than 1 week prior to use in an assay by freezing the pellet to −20° C. after incubation in isotonic saline at 4° C overnight to dialyze out glucose contained in the cells.

Hemolysate was prepared by pelleting enough fresh cells in a screw-capped tube to give 1 ml of packed RBCs. (This step was omitted with frozen RBCs, however, as freezing hemolyses the cells. Instead, the thawed packed cells are used directly for the next step.) To 1 ml of packed RBCs was added 3 ml of distilled water to lyse the cells. Following addition of water, 2 ml of toluene were added to delipidate the suspension. The cells were shaken vigorously for a few minutes, or vortexed intermittently six times to ensure complete lipid extraction. The RBC preparation was then centrifuged at 3000 rpm for 10 rain to separate the two phases and pellet the cellular debris. An interface of white insoluble material is found between the toluene (top) phase and the aqueous (bottom) phase. The toluene phase, above the insoluble material layer overlaying the aqueous hemolysate, was removed using a glass Pasteur pipette with a suction flask. After removing the toluene, the tube was tipped to expose the red aqueous phase underlying the layer of insoluble material. The aqueous phase was removed with a Pasteur pipette, taking care not to disturb either the layer of insoluble material or the pellet at the bottom of the tube. The hemolysate (aqueous phase) was stored overnight at 4° C. if the assay was not to be performed immediately. Long term storage of the hemolysate requires use of a preservative or sterile filtration.

Coating Antigen. BSA-AGE was prepared at 30/µg/ml in a 0.1M bicarbonate buffer, pH 9.6, with azide. One hundred µl of coating solution were incubated in microtiter wells for 1 hr. at 37° C., or overnight at 4° C. Coating solution was washed away and a blocking buffer containing PBS with 0.1 g BSA, 1 ml goat serum and azide was added; the plates were incubated for 1 hr. at 37° C. The plates were washed with a PBS, Tween solution prior to addition of sample.

Microtiter Plate AGE Assay. The hemolysate was diluted in the SDS/Triton/Urea Buffer to give approximately a 1–2 mg/ml concentration of protein. Usually, the hemolysate was diluted 1:40–1:60 to achieve the desired protein concentration range. The protein concentration of the hemolysate was determined using the Lowry procedure (Lowry et al., 1951, J. Biol. Chem. 193:265), with modifications.

Briefly, 3–10 µl of hemolysate preparation were added using an Eppendorf positive displacement pipetter (0.5–10 µl) to a 2–5 ml glass test tube (12×75 mm). To this tube was added 1 ml of Lowry reagent. The sample was mixed well and incubated at room temperature (RT) for 15–30 min. To each tube were added 100 µl of Folin & Ciocalteu's phenol reagent, and the mixture was vortexed immediately in two short intervals. Aggressive or excessive vortexing was avoided to eliminate or reduce abnormal results. The sample was incubated for 30 rain at RT, and optical density read in a dual-beam spectrophotometer at 750 nm against a blank consisting of a mixture of 1 ml of Lowry reagent with 100 µl of the Folin reagent.

A 1 mg/ml BSA (Sigma RIA grade A7888 or A7030) solution in 300 mM $KH_2PO_4$ with 3 mM sodium azide was used as the standard for the protein determination assay. The standard samples were prepared by pipetting 3.12, 6.25, 12 and 25 µl of standard solution into test tubes and performing the assay as described above.

The Lowry reagent, pH 12.8, was prepared by adding 0.5 ml of 2% potassium sodium tartrate ($KNaC_4H_4O_6.H_2O$) and 0.5 ml of 1% $CuSO_4$ to 50 ml of 2% $Na_2CO_3$ in 0.1N NaOH. The Lowry reagent is stable at RT and should not be stored in the refrigerator. Fresh solution was prepared for each assay. Folin & Ciocalteu's phenol reagent was made by dilution of the stock (Sigma F9252) 1:1 with distilled water in an amber glass bottle to yield a 1N solution. This solution was stored at RT.

All samples were either diluted by the same amount, and concentration calculated from the protein concentration, or all hemolysates were adjusted to the same protein concentration (approx. 1 mg/ml) by using an exact ratio of buffer to hemolysate.

To each well of the assay plate were added 50 µl of solution of diluted hemolysate. An additional 50 µl of the SDS/Triton/Urea Buffer was added to each well to normalize the sample.

Preparation of AGE Standard. BSA-AGE for use as a standard was prepared by incubating BSA with glucose in a molar ration of 500:1 glucose:BSA in a phosphate buffer, pH 7.4, for six weeks at 37° C. After the incubation period, the solution was dialyzed against PBS/0.02% azide, and stored at −80° C.

Preparation of Sample Standards. BSA-AGE standards (0.1–3.75 µg/well) were made up in sodium phosphate buffer lacking SDS/Triton/Urea. Fifty µl of each standard was added to assay wells.

Primary Antibody Dilution. Anti-AGE antisera was diluted to give a B50 of 1 µg BSA-AGE. The BSA-AGE was prepared as described above for preparation of the BSA-AGE standard.

Assay Procedure. After coating the microtiter wells with BSA-AGE, 50 µl of sample or standards, diluting buffers, and 50 µl of primary antibody were added to each well. The microtiter plate was incubated for 2 hrs. at room temperature. The microtiter plate was washed 3X with Tris buffered saline (TBS)/Tween. To each well were added 100 µl of alkaline phosphatase labeled secondary antibody at the appropriate titer, and the wells incubated at 37° C. for 1 hr. The microtiter plate was washed 3X with TBS/Tween. Para-nitrophenyl phosphate (PNPP) substrate was added to all wells and incubated for 1–2 hrs until the O.D. of the $B_0$ wells reached 1.7 O.D.

B is the O.D. of binding of labelled antibody in the presence of a sample that contains a competitor. $B_0$ is the signal (O.D.) from control samples without competitor.

Normalization of Values. Immunoassay results (O.D. of sample wells) were expressed as % of $B/B_0$. The AGE concentration was determined from O.D. by extrapolation from a standard curve (see Makita et al., 1992, J. Biol. Chem. 267:5133–38; International Patent Publication No. WO 93/13421).

All sample readings were normalized to the protein concentration, which was determined in the Lowry assay. Thus, the final data are expressed as units of AGE per mg of hemoglobin.

Results and Discussion

A much simpler and reproducible Hb-AGE ELISA assay, with greater sensitivity due to what is believed to be maximal exposure of AGE epitopes, has been developed. The new assay includes incubation of samples containing hemoglobin with SDS, Triton X-100, and urea.

In preliminary experiments, it was found that incubation with SDS alone enhanced detection of hemoglobin-AGE. However, SDS alone altered the standard assay conditions, and affected the binding of anti-AGE antibody to the AGE-model dipeptide, Gly-Lys browned with ribose, compared to binding in the absence of SDS.

After further experimentation, it was found that the assays of samples pretreated only with SDS could be improved by including an optimal combination of Triton X-100 and urea in the dilution buffer. The optimal concentrations of SDS/Triton/urea were empirically found to be 0.08%/0.01%/2M in rat samples and 0.08%/0.04 %/2M in human samples, respectively. Neither of the above sample diluents, 0.08% SDS/0.01% Triton/2M Urea used for rat samples or 0.08% SDS/0.04% Triton/2M urea used for human samples, induced detachment or elution of the coated BSA-AGE antigen from the well (data not shown).

Using the newly developed assay pretreatment method, significant differences in the level of hemoglobin-AGE were observed between normal patients and diabetics (FIG. 1A). Similar data are observed in samples from normal rats and rats with induced diabetes (FIG. 1B).

The present assay method for Hb-AGE shows good correlation with $Hb-A_{1c}$ in normal and diabetic humans (FIG. 2). Thus, Hb-AGE is as effective a marker as $Hb-A_{1c}$ for diagnosis of AGE-associated diseases, such as diabetes.

With the newly modified method, the inhibitory effect of aminoguanidine on the Hb-AGE content in vivo from samples in a rat assay was clearly demonstrated (FIG. 3). Hemoglobin-AGE is a much more relevant marker for the aminoguanidine effect than $Hb-A_{1c}$, since the latter is not affected by the presence of aminoguanidine, or other AGE-inhibitors, at their pharmaceutically relevant concentration.

Using the method of the present invention, delipidated hemolysates can be diluted down to around 1–2 mg/ml of protein, which consists mostly of hemoglobin. For example, the samples shown in FIGS. 1, 2, and 3 were diluted 40 fold before addition to the assays. One possible explanation for this increased sensitivity is that the SDS/Triton/Urea pretreatment exposes Hb-AGE epitopes that would otherwise be inaccessible to antibody binding in the ELISA or other immunoassay.

This invention may be embodied in other forms or carded out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various references are cited throughout this specification, each of which is incorporated herein by reference in its entirety.

What is claimed is:

1. A method for detecting the presence of hemoglobin-advanced glylosylation end-products, hemoglobin-AGE, in a sample comprising:
   a) diluting the sample in a dilution buffer, which dilution buffer comprises sodium dodecyl sulfate at a concentration sufficient to denature hemoglobin-AGE;
   b) contacting the diluted sample with a binding partner of an AGE; and
   c) detecting the presence of hemoglobin-AGE in the sample by detecting binding of the binding partner of an AGE to hemoglobin-AGE.

2. The method according to claim 1, wherein the dilution buffer further comprises:
   i) a non-ionic surfactant at a concentration sufficient to facilitate detection of hemoglobin-AGE wherein the concentration of non-ionic surfactant ranges from about 0.005% to about 0.1% (w/v); and ii) a denaturing agent at a concentration sufficient to denature hemoglobin-AGE and increase assay sensitivity, without interfering with the binding of the binding partner of an AGE to hemoglobin-AGE.

3. The method according to claim 1 wherein concentration of sodium dodecyl sulfate ranges from about 0.04% to about 0.16% (w/w).

4. The method according to claim 2 wherein the non-ionic surfactant is a polyoxyethylene ester.

5. The method according to claim 2 wherein the concentration of the denaturing agent is between about 0.5M to about 3M.

6. The method according to claim 5 wherein the denaturing agent is urea.

7. The method according to claim 1 wherein the dilution buffer is buffered to between about pH 7 to about pH 8, and contains salts at a concentration approximating physiological ionic strength.

8. The method according to claim 1, wherein the binding partner of an AGE is an antibody.

9. A method for detecting the presence of hemoglobin-AGE in a sample comprising:
   a) diluting the sample in a diluent buffer, which diluent buffer comprises
      i) sodium dodecyl sulfate at a concentration of from about 0.04% to about 016% (w/v);
      ii) polyoxyethylene ester at a concentration of from about 0.005% to about 0.1% (w/v); and
      iii) urea at a concentration of between about 0.5M to about 3M;
   b) contacting the diluted sample with a binding partner of an AGE; and
   c) detecting the presence of hemoglobin-AGE in the sample by detecting binding of the binding partner of an AGE to hemoglobin-AGE.

10. The method according to claim 9 wherein the concentration of sodium dodecyl sulfate is about 0.08%, the concentration of polyoxyethylene ester is selected from the group consisting of about 0.01% and about 0.04%, and the concentration of urea is about 2M.

11. The method according to claim 9 wherein the dilution buffer is buffered to between about pH 7 to about pH 8, and contains salts at a concentration approximating physiological ionic strength.

12. A method for quantitating the amount or level of hemoglobin-AGE in a sample comprising:
   a) detecting the presence of hemoglobin-AGE in the sample according to the method of claim 1, 2 or 9; and
   b) quantitating the extent of detection of hemoglobin-AGE in the sample;
in which the extent of detection corresponds to the amount of hemoglobin-AGE in the sample.

13. A method for indicating the presence of a disease associated with elevated hemoglobin-AGE levels in a mammalian subject comprising:
   (a) quantitating the amount of hemoglobin-AGE in a sample from a mammalian subject according to claim 12; and
   (b) comparing the level detected in step (a) to a level of hemoglobin-AGE normally present in the mammalian subject;
in which an increase in the level of hemoglobin-AGE as compared to normal levels indicates a disease associated with elevated levels of hemoglobin-AGE.

14. A method for monitoring the course of a disease associated with elevated hemoglobin-AGE levels in a mammalian subject comprising evaluating an amount of hemoglobin-AGE in a series of samples obtained at different time points from a mammalian subject, wherein the amount of hemoglobin-AGE is quantitated according to the method of claim 12, in which an increase in the level of hemoglobin-AGE over time indicates progression of the disease, and in which a decrease in the level of hemoglobin-AGE over time indicates regression of the disease.

15. A method for monitoring a therapeutic treatment of a disease associated with elevated hemoglobin-AGE levels in a mammalian subject comprising evaluating the level of hemoglobin-AGE in a series of samples obtained at different time points from a mammalian subject undergoing a therapeutic treatment for a disease associated with elevated hemoglobin-AGE levels, wherein the level of hemoglobin-AGE is quantitated according to the method of claim 12, in which a decrease in the level of hemoglobin-AGE over time indicates an effective therapeutic outcome.

16. A method for determining the optimum dosage of an inhibitor of advanced glycosylation endproduct formation in a mammalian subject with elevated levels of hemoglobin-AGEs comprising evaluating the level of hemoglobin-AGE in a series of samples obtained at different time points from a mammalian subject receiving progressively larger doses of an inhibitor of AGE formation over the time points, wherein the level of hemoglobin-AGE is quantitated according to the method of claim 12, and wherein an optimum dosage of the inhibitor is a dosage above which no further decrease in the level of hemoglobin-AGE is observed.

17. A method for monitoring the long term glucose level in a mammalian subject comprising evaluating the level of hemoglobin-AGE in a sample from a mammalian subject, wherein the level of hemoglobin-AGE is quantitated according to the method of claim 12, and wherein the level of hemoglobin-AGE is indicative of the long term glucose level.

18. The method according to claim 9, wherein the binding partner of an AGE is an antibody.

19. A kit for detecting the presence of hemoglobin-AGE in a sample comprising:
   a) a dilution buffer comprising sodium dodecyl sulfate in concentrated or ready-to-use form, wherein the sodium dodecyl sulfate is used at a concentration sufficient to denature hemoglobin-AGE without interfering in binding of reagents with hemoglobin-AGE;
   b) a binding partner of an AGE for detecting the presence of hemoglobin-AGE; and
   c) directions for use of said kit.

20. The kit of claim 19, wherein the dilution buffer further comprises:
   i) a non-ionic surfactant at a concentration sufficient to facilitate detection of hemoglobin-AGE wherein the concentration of non-ionic surfactant ranges from about 0.005% to about 0.1% (w/v); and
   ii) a denaturing agent at a concentration sufficient to denature hemoglobin-AGE and increase assay sensitivity, without interfering with the binding of reagents to hemoglobin-AGE.

21. The kit of claim 20, wherein the concentration of sodium dodecyl sulfate ranges from about 0.04% to about 0.16% (w/v); the concentration of non-ionic surfactant ranges from about 0.005% to about 0.1% (w/v); and the concentration of the denaturing agent is between about 0.5M to about 3M.

22. The kit of claim 21, wherein the non-ionic surfactant is polyoxyethylene ester, and the denaturing agent is urea.

23. The kit of claim 22, wherein the concentration of sodium dodecyl sulfate is about 0.08%, the concentration of polyoxyethylene ester is selected from the group consisting of about 0.01% and about 0.04%, and the concentration of urea is about 2M.

24. The kit of claim 23, wherein the dilution buffer is buffered to between about pH 7 and about pH 8, and contains salts at a concentration approximating physiological ionic strength.

25. The kit of claim 19, 20, 21, 22, 23, or 24, wherein the binding partner of an AGE is an antibody.

* * * * *